United States Patent
Themelis

(10) Patent No.: US 11,156,820 B2
(45) Date of Patent: Oct. 26, 2021

(54) METHOD FOR FLUORESCENCE INTENSITY NORMALIZATION

(71) Applicant: LEICA INSTRUMENTS (SINGAPORE) PTE. LTD., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 93 days.

(21) Appl. No.: 16/251,131

(22) Filed: Jan. 18, 2019

(65) Prior Publication Data
US 2019/0227288 A1 Jul. 25, 2019

(30) Foreign Application Priority Data
Jan. 19, 2018 (EP) .................................. 18152617

(51) Int. Cl.
*G02B 21/00* (2006.01)
*G02B 21/36* (2006.01)
(Continued)

(52) U.S. Cl.
CPC ........ *G02B 21/008* (2013.01); *A61B 1/00188* (2013.01); *A61B 1/043* (2013.01);
(Continued)

(58) Field of Classification Search
CPC ........ G02B 5/208; G02B 5/0891; G02B 5/09; G02B 1/04; G02B 26/0833; G02B 5/223;
(Continued)

(56) References Cited

U.S. PATENT DOCUMENTS

| 6,791,618 B1 | 9/2004 | Shimizu |
| 2002/0098588 A1 | 7/2002 | Sammak et al. |

(Continued)

FOREIGN PATENT DOCUMENTS

| EP | 2081072 A1 | 7/2009 |
| JP | H06265795 A | 9/1994 |

(Continued)

OTHER PUBLICATIONS

"Molecular Expressions Microscopy Primer: Photomicrography—Fluorescence Microscopy Errors," Nov. 2015, retrieved from Internet, <https //micro.magnet.fsu.edu/primer/photomicrography/fluorescenceerrors.html>.

(Continued)

*Primary Examiner* — William R Alexander
*Assistant Examiner* — Sharrief I Broome
(74) *Attorney, Agent, or Firm* — Hodgson Russ LLP

(57) ABSTRACT

The invention relates to a method, in particular a fluorescence microscopy or endoscope imaging method for intensity normalization, a non-transient computer readable storage medium (101) and a controller (51) for an endoscope (3) or microscope device (5). In the prior art, common observation devices (1) as surgical microscopes, endoscopes (3) or microscopes (5) have the disadvantage that it is ambiguous whether a detected intensity (97) is due to fluorophore (29) concentration or due to optics setting parameters (73). The inventive method overcomes said disadvantages by automatically adjusting at least one exposure control parameter (83) if at least one optics setting parameter (73) is changed. The inventive non-transient computer readable storage medium (101) is adapted to run a program for executing the inventive method and the inventive controller (51) comprises an input section (67) for receiving optics setting data (71); an output section (69) for outputting (Continued)

exposure control data (81); and a determination module (53) for determining at least one exposure control data (81) dependent on at least one optics setting data (71).

16 Claims, 1 Drawing Sheet

(51) Int. Cl.
*G06T 7/80* (2017.01)
*A61B 1/00* (2006.01)
*A61B 1/04* (2006.01)
*A61B 1/045* (2006.01)
*G02B 21/02* (2006.01)
*G02B 23/24* (2006.01)

(52) U.S. Cl.
CPC .......... *A61B 1/045* (2013.01); *G02B 21/0076* (2013.01); *G02B 21/025* (2013.01); *G02B 21/365* (2013.01); *G06T 7/80* (2017.01); *G02B 23/2484* (2013.01); *G06T 2207/10064* (2013.01)

(58) Field of Classification Search
CPC ...... G02B 1/10; G02B 5/0284; G02B 5/1809; G02B 13/0045; G02B 13/143; G02B 19/0023; G02B 19/0042; G02B 19/0095; G02B 1/11; G02B 1/115; G02B 1/118; G02B 1/14; G02B 27/0006; G02B 27/0988; G03F 7/702; G03F 7/70075; G03F 7/70116; G03F 7/7015; G03F 7/70233; G03F 7/70316; G03F 7/70958; G03F 7/70083; G03F 7/70191; G03F 7/70291; G03F 7/70566; G03F 7/70825; G03F 7/70891; G03F 1/24; G03F 1/52; G03F 1/84; G03F 7/0007; G03F 7/0757; G03F 7/2059; G03F 7/40; H01L 2924/0002; H01L 27/14618; H01L 2924/00; H01L 27/14625; H01L 31/056; H01L 31/0232; H01L 31/02325; H01L 31/052; H01L 21/02422; H01L 21/02532; H01L 21/02554; H01L 21/02565; H01L 21/02601; H01L 21/02628; H01L 21/67109; H01L 21/67115; H01L 2224/13; H01L 27/14621; H01L 27/14623; H01L 27/14627; B32B 17/10036; B32B 17/10229; B32B 2307/40; B32B 2307/412; B32B 2307/71; B32B 27/08; B32B 37/12; B32B 7/02; B32B 7/12; B32B 17/06; B32B 17/064; B32B 17/10; B32B 17/10174; B32B 17/1022; B32B 17/10247; B32B 17/10293; B32B 17/10467; B32B 17/10504; B32B 17/10532; B32B 17/10761

See application file for complete search history.

(56) References Cited

U.S. PATENT DOCUMENTS

| | | | |
|---|---|---|---|
| 2003/0016301 A1 | 1/2003 | Aizaki et al. | |
| 2008/0083754 A1 | 4/2008 | Robinson | |
| 2009/0168156 A1* | 7/2009 | Ariga | G02B 21/365 |
| | | | 359/381 |
| 2009/0309963 A1* | 12/2009 | Ogihara | H04N 5/235 |
| | | | 348/79 |
| 2013/0294645 A1* | 11/2013 | Sibarita | G06T 7/11 |
| | | | 382/103 |
| 2015/0130920 A1* | 5/2015 | Zou | G02B 21/245 |
| | | | 348/79 |
| 2017/0235118 A1* | 8/2017 | Kuster | G02B 21/16 |
| | | | 600/476 |
| 2018/0003941 A1* | 1/2018 | Stauffer | H04N 5/23222 |
| 2018/0146844 A1 | 5/2018 | Okazaki et al. | |
| 2019/0099081 A1* | 4/2019 | Horesh | A61B 1/043 |

FOREIGN PATENT DOCUMENTS

| | | |
|---|---|---|
| JP | H0821956 A | 1/1996 |
| JP | 2003076981 A | 3/2003 |
| JP | 2005156651 A | 6/2005 |
| JP | 2011007642 A | 1/2011 |
| JP | 2013257423 A | 12/2013 |
| WO | 2016123300 A1 | 8/2016 |

OTHER PUBLICATIONS

Sanderson, Micheal J. et al, "Fluorescence Microscopy", Cold Spring Harbor Protocols, Oct. 1, 2014, vol. 10, 36 pages.

* cited by examiner

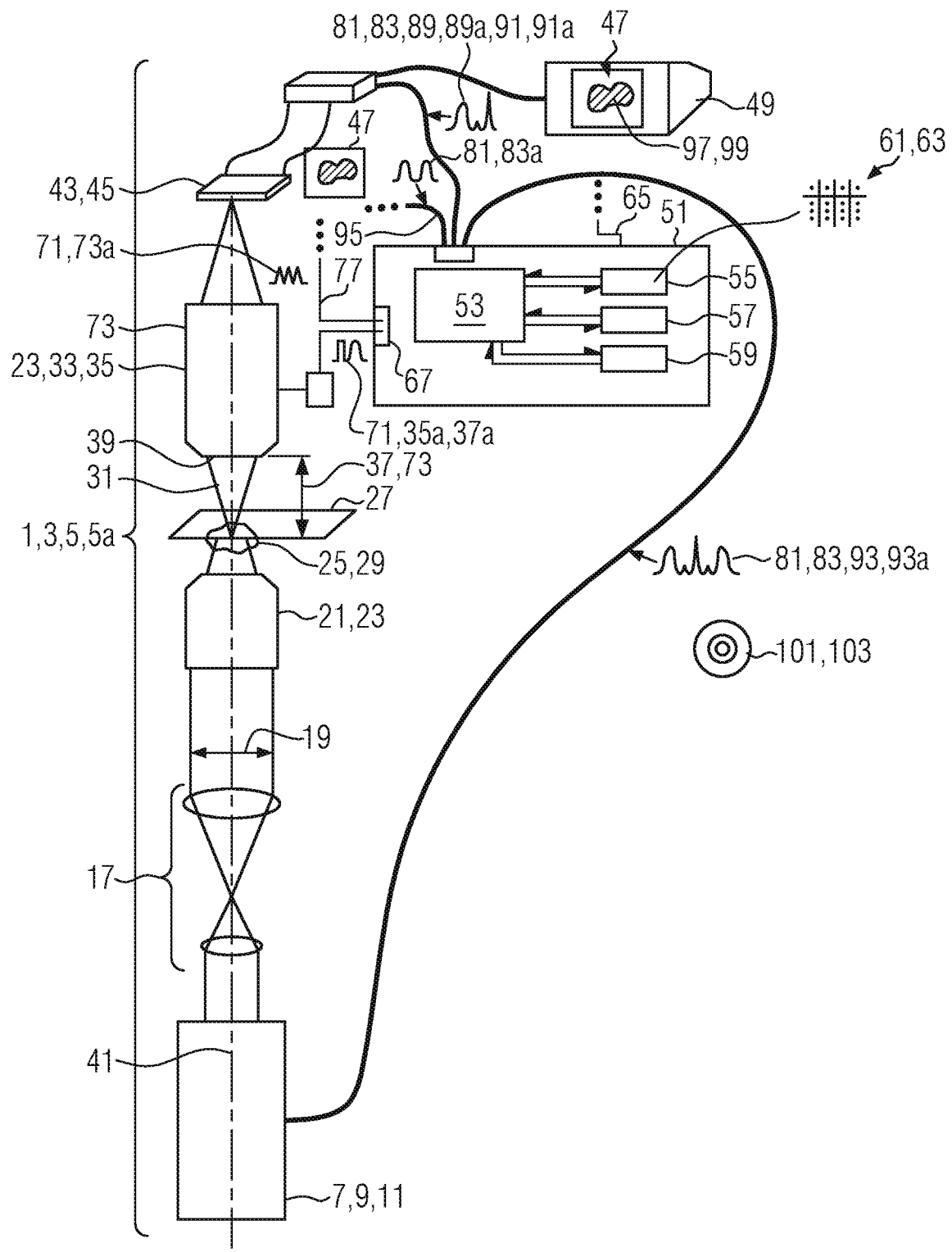

METHOD FOR FLUORESCENCE INTENSITY NORMALIZATION

CROSS REFERENCE TO RELATED APPLICATIONS

This application claims priority of European patent application number 18152617.9 filed Jan. 19, 2018, the entire disclosure of which is incorporated by reference herein.

FIELD OF THE INVENTION

The invention relates to a method, in particular a fluorescence microscopy or endoscope imaging method for intensity normalization, a non-transient computer readable storage medium and a controller for an endoscope or microscope device.

BACKGROUND OF THE INVENTION

In the prior art, common observation devices as surgical microscopes, endoscopes or microscopes have the disadvantage that a measured intensity, in particular during an observation based on fluorescence, i.e. a fluorescence intensity, is affected by optics setting parameters of the observation device. In general, a sensitivity of known observation devices shows a functional relationship with the optics setting parameters. The sensitivity may for instance be inversely proportional to at least one of the optics setting parameters.

Therefore, great care has to be taken if the fluorescence intensity is imaged, as it is ambiguous whether the detected intensity is due to fluorophore concentration or due to optics setting parameters.

SUMMARY OF THE INVENTION

An object of the present invention is therefore to provide a method, a non-transitory storage medium and a controller for an endoscope or microscope device which improve the determination of a fluorophore concentration.

The inventive method mentioned in the beginning solves the above problem and overcomes the drawbacks of prior art methods by automatically adjusting at least one exposure control parameter if at least one optics setting parameter is changed.

The inventive non-transient computer readable storage medium comprises a program for executing at least one embodiment of the inventive method, and thus yields the same advantages as the inventive method.

The inventive controller mentioned in the beginning solves the above problems by comprising an input section for receiving optics setting data representing optics setting parameters. The optics setting data in particular comprise at least one of magnification setting data and working-distance setting data and the controller further has an output section for outputting exposure control data representing exposure control parameters. The exposure control data in particular comprise at least one of the group comprising detector gain data, exposure time data and light intensity data.

Furthermore, the controller has a determination module for determining at least one exposure control data dependent on at least one optics setting data.

The inventive method, the inventive non-transient computer readable storage medium and the inventive controller allow counterbalancing the effect of at least one varied optics setting parameter of the observation device, wherein without counterbalancing a changed intensity, in particular fluorescence intensity, would be measured despite the same fluorophore concentration in the examined sample.

Therefore, the influence of changing optics setting parameters on the detected intensity (fluorescence intensity) is eliminated and a constant (fluorescence) intensity of the observed sample will result in a constant intensity value or brightness in the image data or as observed by the user through observation means (e.g. ocular), respectively.

The adjustment of the observation device is in particular performed automatically, i.e. without the need of user interaction.

The present invention may be improved by further embodiments, which are advantageous on their own. Technical features of the different embodiments may be arbitrarily combined with each other or may be omitted, if the omitted technical feature is not essential for achieving the inventive technical effect.

The term "determination" or "to determine" is to be understood as to find or identify a position, magnitude or value and not as to fix, define or specify a position, magnitude or value.

In the following description, expressions as fluorescence intensity, microscopes or endoscopes or specific optics setting parameters or exposure control parameters are not to be understood to limit the present invention. Those expressions are rather to be understood as representatives for intensity, optical observation devices and the entirety of optics setting or exposure control parameters. Similarly, singular or plural forms do not limit the scope of protection.

The inventive method may in particular use calibration data to automatically adjust the at least one exposure control parameter depending on the at least one optics setting parameter.

The corresponding inventive controller which is adapted to perform this embodiment of the inventive method may therefore comprise at least one memory module with previously saved calibration data.

The calibration data may be understood as a look-up table which interrelates or links at least one optics setting parameter with at least one exposure control parameter. In particular, the calibration data assigns an exposure control parameter or a combination of exposure control parameters to an optics setting parameter or a combination of optics setting parameters.

The calibration data may therefore be understood as predetermined values saved in form of an assignment table.

The inventive method may further comprise computing the at least one exposure control parameter based on the at least one optics setting parameter.

The corresponding inventive controller may therefore comprise a computing module for computation of the at least one exposure control data based on the at least one optics setting data.

Computing of the at least one exposure control parameter may be performed additionally or alternatively to the assignment based on previously saved calibration data.

Particularly if the at least one optics setting parameter is not provided in the calibration data, the computing module may be used to compute the at least one exposure control parameter based on the at least one optics setting parameter, which is provided via the input section of the controller.

In a further embodiment an interpolation module may be provided in the controller. A corresponding method may therefore comprise the step of interpolating the at least one exposure control data based on the at least one optics setting data.

The optics setting parameters may comprise a working distance and/or a magnification. They may also comprise a parameter representing the objective used.

Different objectives may yield a different optical grade and may therefore alter the detected fluorescence intensity.

The working distance may be understood as a measured distance between a front end of a detection optics assembly for collecting the light, for example the fluorescence light from the sample, and a detection plane in which the sample is arranged. The detection optics assembly may be an objective.

Consideration of the optics setting parameters, which are provided to the controller in form of optics setting data, are consequently applied to determine, i.e. assign and/or calculate exposure control parameters, which are output from the controller in form of exposure control data, such that a change of detected intensity, in particular fluorescence intensity due to different optics settings is prevented, as it is counterbalanced by the inventive method and inventive controller.

Therefore, the influence of an optical system, in particular an optical detection system such as an objective on the detected intensity, is automatically eliminated.

The at least one exposure control parameter may in particular be proportional to the at least one optics setting parameter.

The exposure control parameters may comprise at least one of the group comprising a detector gain, an exposure time and a light intensity. Said group is not to be understood as being closed, and further parameters may be comprised within the group of exposure control parameters.

In other words, the value of an exposure control data representing one exposure control parameter (e.g. the detector gain) may increase if the value of an optics settings data, representing one optics setting parameter (e.g. the magnification), is increased.

A sensitivity of the observation device comprising the inventive controller, or performing the inventive method, may therefore be inversely proportional to the at least one optics setting parameter The sensitivity may be understood as a minimum magnitude of a signal input to a detector, which is required to generate a specific and in particular detectable output signal. Exemplarily, the sensitivity of the detector in an observation device may be defined as a certain number of photons of the light to be detected that need to be incident on a defined detector surface to generate a detectable electrical signal.

Particular settings, e.g. a large working distance, may reduce the number of photons incident on the defined detector surface below a sensitivity threshold and may render a fluorescence signal undetectable. The inventive method and the inventive controller counterbalance a reduction of the intensity and prevent a flourescence signal from becoming undetectable.

The inventive non-transient computer readable storage medium may be embodied as a magnetic, optical or flash-memory-based storage medium.

The controller may be embodied in one single integrated circuit (IC) or may be assembled from separate parts like the determination module, the memory module and/or the computation module.

The memory module and/or the computation module may be replaceable, such that the controller may be applied in a different observation device, wherein calibration data stored in the memory module and/or a calculation formula stored and executed in the computation module may be easily replaced and adapted to the different observation device.

In the following, the present invention will be described with reference to the accompanied FIGURE. The embodiment shown in the FIGURE is to be understood as purely exemplary, i.e. not limiting the scope of protection, which is defined by the claims. The technical features described with the embodiment shown in the FIGURE may be arbitrarily combined and/or omitted in compliance with the accompanied claims. The same technical features and technical features having the same technical effect are denoted with the same reference numeral.

BRIEF DESCRIPTION OF THE DRAWING VIEW

FIG. 1 shows a schematic drawing of an optical observation device comprising an inventive controller.

DETAILED DESCRIPTION OF THE INVENTION

FIG. 1 schematically shows an observation device 1, such as an endoscope device 3 or microscope device 5, wherein the microscope device 5 may in particular be embodied as a fluorescence microscope 5a.

The fluorescence microscope 5a comprises a light source 7, which may in particular be embodied as a laser 9, preferably a semiconductor laser 11, which emits illumination light 15 that passes through a telescope 17 for increasing a beam waist 19.

The illumination light 15 passes an optical illumination assembly 21 which is embodied as an objective 23.

The optical illumination assembly 21 transmits the illumination light 15 which illuminates a sample 25 which is arranged in a detection plane 27.

The sample 25 comprises fluorophores 29 (not shown separately), which are excited by the incident illumination light 15 and which emit fluorescence light 31.

The fluorescence light 31 is collected by a detection optics assembly 33 which is also embodied as an objective 23.

The detection optics assembly 33 is characterized by a magnification 35 and is arranged within a working distance 37 from the detection plane 27.

The working distance 37 is measured from the detection plane 27 to a front end 39 of the detection optics assembly 33.

It is noted that the microscope 5a shown in FIG. 1 is embodied linearly, i.e. the light source 7, the optical illumination assembly 21 and the detection optics assembly 33 are arranged along one and the same optical axis 41. In different embodiments, a path of the illumination light 15 may be oriented essentially perpendicular to a path of the fluorescence light 31, that is, a configuration of the fluorescence microscope 5a may correspond to the configuration of a so-called single plane illumination microscope or briefly SPIM.

The fluorescence light 31 is transmitted through the detection optics assembly 33 and imaged onto a detector 43, which may be embodied as a two-dimensional CCD or CMOS sensor 45.

The detection optics assembly 33 therefore images a fluorescence image 47 (schematically shown) onto the detector 43.

The fluorescence image 47 may be shown on a viewer 49, which may also additionally or alternatively be embodied as an ocular (not shown).

The fluorescence microscope 5a further comprises a controller 51 having a determination module 53, a memory module 55, an interpolation module 57 and a to computing module 59.

The modules 55, 57, 59 are connected to the determination module 53, wherein data may be exchanged between them in both directions.

The memory module 55 comprises calibration data 61, which may be embodied as a look-up table 63, which is schematically indicated by a table in FIG. 1. The calibration data 61 may be saved in the memory module 55 by providing them at a calibration data input 65 provided at the controller 51

The controller 51 further comprises an input section 67 and an output section 69, wherein the controller 51 receives optics setting data 71 via the input section 67.

The optics setting data 71 are indicated by a sequence of electronic rectangular pulses, wherein this shape is exemplary and not limiting the form in which the optics setting data 71 is provided.

The optics setting data 71 represent optics setting parameters 73 such as the magnification 35 of the detection optics assembly 33 and the working distance 37 in the form of magnification setting data 35a and working-distance setting data 37a, respectively.

Those exemplary two optics setting parameters 73 are provided to the input section 67 of the controller 51 via an objective control module 75.

FIG. 1 furthermore shows an additional input line 77 which is embodied to provide optics setting data 71 representing a different optics setting parameter 73a to the controller 51 than those shown in FIG. 1. The optics setting data 71 are indicated by pulses with a triangular shape for distinction.

Via the output section 69, the controller 51 outputs exposure control data 81.

The exposure control data 81 are indicated by a sequence of electronic pulses, wherein also their shape is exemplary and not limiting the form in which the exposure control data 81 is provided by the controller 51.

The exposure control data 81 represent exposure control parameters 83 such as a detector gain 89, an exposure time 91 or a light intensity 93 of the light source 7, which are represented by detector gain data 89a, exposure time data 91a and light intensity data 93a, respectively.

Those exemplary three exposure control parameters 83 are provided by the controller 51 at the output section 69, whereas the controller 51 comprises an additional output line 95 which is embodied to provide exposure control data 81 representing a different exposure control parameter 83a to the controller 51 which differs from those shown in FIG. 1. The exposure control data 81 are indicated by pulses with a Gaussian shape for distinction.

The controller 51 therefore receives the optics setting data 71 which represent the optics setting parameters 73, in particular comprising at least one of magnification setting data 35a and working-distance setting data 37a, and determines at least one exposure control data 81 based on said optics setting data 71. This determination is either based on an assignment using the calibration data 61 in the memory module 55 or based on a calculation performed in the computing module 59.

If the calibration data 61 does not comprise the exact optics setting data 71, the interpolation module 57 may interpolate the exposure control data 81 to be output by the controller 51 via the output section 69.

Consequently, a light intensity 97, which is for instance represented by a brightness 99 of the fluorescence image 47 shown in the viewer 49, remains constant, even if particular optics setting parameters 73 are modified.

The exposure control data 81 output by the controller 51 may comprise one or a combination of control data 83a, 89a, 91a and 93a.

The inventive method performed by the fluorescence microscope 5a shown in FIG. 1 may be embodied as a software implementation, i.e. in the form of a program stored on a non-transitory storage medium 101, as shown in FIG. 1 in the embodiment of a CD-ROM 103.

REFERENCE SIGNS 1 observation device
3 endoscope device
5 microscope device
5a fluorescence microscope
7 light source
9 laser
11 semiconductor laser
15 illumination light
17 telescope
19 beam waist
21 optical illumination assembly
23 objective
25 sample
27 detection plane
29 fluorophore
31 fluorescence light
33 detection optics assembly
35 magnification
35a magnification setting data
37 working distance
37a working-distance setting data
39 front end
41 optical axis
43 detector
45 two-dimensional CCD or CMGS sensor
47 fluorescence image
49 viewer
51 controller
53 determination module
55 memory module
57 interpolation module
59 computing module
61 calibration data
63 look-up table
65 calibration data input
67 input section
69 output section
71 optics setting data
73 optics setting parameter
73a different optics setting parameter
75 objective control module
77 additional input line
81 exposure control data
83 exposure control parameter
83a different exposure control parameter
89 detector gain
89a detector gain data
91 exposure time
91a exposure time data
93 light intensity
93a light intensity data
95 additional output line 97 light intensity
99 brightness
101 non-transitory storage medium
103 CD-ROM

What is claimed is:

1. A method of intensity normalization for imaging carried out by an observation device (1) configured to image a sample (25) positioned in a detection plane (27), the observation device (1) having a light source (7), a detection optics assembly (33) settable at a working distance (37) from the detection plane (27), an image detector (43), and a viewer (49) in which an image (47) of the sample (25) is shown, the method comprising:

changing at least one optics setting parameter (73) of the observation device (1), wherein the at least one optics setting parameter includes the working distance (37); and automatically adjusting a plurality of exposure control parameters (83) of the observation device (1) in response to the step of changing at least one optics setting parameter (73), wherein the plurality of exposure control parameters includes a light intensity (93) of the light source (7) and a detector gain (89) of the image detector (43);

whereby a brightness (99) of the image (47) shown in the viewer (49) remains constant if the at least one optics setting parameter (73) is changed.

2. The method according to claim 1, wherein calibration data (61) are used to automatically adjust the at least one exposure control parameter (83) depending on the at least one optics setting parameter (73).

3. The method according to claim 1, wherein the method further comprises computing the at least one exposure control parameter (83) based on the at least one optics setting parameter (73).

4. The method according to claim 1, wherein the at least one optics setting parameter (73) further includes a magnification (35) of the observation device (1).

5. The method according to claim 1, wherein the at least one exposure control parameter (83) is proportional to the at least one optics setting parameter (73).

6. The method according to claim 1, wherein the at least one exposure control parameter (83) further includes an exposure time (91) of the image detector (43).

7. The method according to claim 1, wherein the observation device is a microscope.

8. The method according to claim 7, wherein the microscope is a fluorescence microscope.

9. The method according to claim 1, wherein the observation device is an endoscope.

10. A non-transient computer readable storage medium (101) comprising a program for executing the method according to claim 1.

11. An observation device (1) for imaging a sample (25) positioned in a detection plane (27), the sample (25) comprising fluorophores (29), the observation device (1) comprising:

a light source (7) for illuminating the sample (25) with incident illumination light (15) exciting the fluorophores (29) and causing the fluorophores (29) to emit fluorescence light (31);

an image detector (43) having exposure control parameters (83);

a detection optics assembly (33) having optics setting parameters (73), wherein the detection optics assembly (33) receives the fluorescence light (31) and images a fluorescence image (47) of the sample (25) onto the image detector (43);

a viewer (49) in which the fluorescence image (47) of the sample (25) is shown; and a controller (51) comprising:

an input section (67) configured to receive optics setting data (71) representing the optics setting parameters (73) of the detection optics assembly (33), the optics setting data (71) comprising at least one of magnification setting data (35a) representing a magnification setting of the detection optics assembly (33) and working-distance setting data (37a) representing a distance from the detection plane (27) at which the detection optics assembly is set;

an output section (69) configured to output exposure control data (81) representing exposure control parameters (83) of the observation device (1), the exposure control data (81) comprising at least one of detector gain data (89a) representing a detector gain (89) of the image detector (43), exposure time data (91a) representing an exposure time (91) of the image detector (43), and light intensity data (93a) representing a light intensity of the light source (7); and a determination module (53) configured to determine the exposure control data (81) dependent on the optics setting data (71) such that a brightness (99) of the fluorescence image (47) imaged on the image detector (43) and shown in the viewer (49) remains constant if at least one of the optics setting parameters (73) is changed.

12. The observation device (1) according to claim 11, wherein the controller (51) further comprises at least one memory module (55) having calibration data (61) stored therein.

13. The observation device (1) according to claim 11, wherein the controller (51) further comprises a computing module (59) configured to compute the exposure control data (81) based on the optics setting data (71).

14. The observation device (1) according to claim 12, wherein the calibration data (61) includes a look-up table that interrelates at least one of the optics setting parameters (73) with at least one of the exposure control parameters (83), and the exposure control data (81) is automatically determined using the calibration data (61).

15. The observation device (1) according to claim 11, wherein the observation device (1) is a fluorescence microscope.

16. The observation device (1) according to claim 11, wherein the observation device (1) is an endoscope.

* * * * *